(12) United States Patent
Song et al.

(10) Patent No.: US 11,064,975 B2
(45) Date of Patent: Jul. 20, 2021

(54) ULTRASONIC PROBE

(71) Applicant: SAMSUNG MEDISON CO., LTD., Gangwon-do (KR)

(72) Inventors: In Seong Song, Daegu (KR); Won-Soon Hwang, Hanam-si (KR)

(73) Assignee: SAMSUNG MEDISON CO., LTD., Gangwon-do (KR)

( * ) Notice: Subject to any disclaimer, the term of this patent is extended or adjusted under 35 U.S.C. 154(b) by 296 days.

(21) Appl. No.: 15/260,153

(22) Filed: Sep. 8, 2016

(65) Prior Publication Data

US 2017/0112469 A1  Apr. 27, 2017

(30) Foreign Application Priority Data

Oct. 27, 2015 (KR) .................. 10-2015-0149107

(51) Int. Cl.
*A61B 8/00* (2006.01)

(52) U.S. Cl.
CPC .............. *A61B 8/4444* (2013.01); *A61B 8/44* (2013.01); *A61B 8/4405* (2013.01); *A61B 8/4483* (2013.01); *A61B 2562/187* (2013.01)

(58) Field of Classification Search
CPC ... A61B 8/4444; A61B 8/00; A61B 2562/187; A61B 8/4405; A61B 8/44; A61B 8/4483; A61B 2562/164; A61B 8/4466; A61B 8/445; A61B 8/4461; A61B 8/46; A61B 8/4272; A61B 8/4455
See application file for complete search history.

(56) References Cited

U.S. PATENT DOCUMENTS

| | | | | |
|---|---|---|---|---|
| 4,011,747 A | * | 3/1977 | Shaw ...................... | G10K 11/32 73/618 |
| 4,092,867 A | * | 6/1978 | Matzuk .................... | A61B 8/00 600/445 |
| 4,149,419 A | * | 4/1979 | Connell, Jr. ............. | A61B 8/00 73/621 |
| 4,399,822 A | * | 8/1983 | Theumer .................. | A61B 8/00 600/445 |
| 4,913,158 A | * | 4/1990 | Kikuchi ............... | G10K 11/355 600/446 |

(Continued)

FOREIGN PATENT DOCUMENTS

| | | | |
|---|---|---|---|
| CN | 103181784 A | 7/2013 | |
| JP | 2003-038489 A | 2/2003 | |
| WO | WO-2018019974 A1 * | 2/2018 | ........... G10K 11/002 |

OTHER PUBLICATIONS

Extended European Search Report dated Mar. 2, 2017 issued in European Patent Application No. 16183093.0.

(Continued)

*Primary Examiner* — Luther Behringer
*Assistant Examiner* — Amy J Shafqat
(74) *Attorney, Agent, or Firm* — Morgan, Lewis & Bockius LLP

(57) ABSTRACT

Disclosed is an ultrasonic probe in which a supporting member is provided with a buffer unit to mitigate an outside impact. The ultrasonic probe includes a transducer rotatably provided, a shaft having the transducer mounted thereto, and a supporting member rotatably supporting the shaft, wherein the supporting member is provided with a buffer unit to mitigate an outside impact.

12 Claims, 16 Drawing Sheets

(56) References Cited

U.S. PATENT DOCUMENTS

| | | | | |
|---|---|---|---|---|
| 5,048,529 A | * | 9/1991 | Blumenthal | G10K 11/355 600/446 |
| 5,088,495 A | * | 2/1992 | Miyagawa | G10K 11/355 600/446 |
| 5,329,194 A | * | 7/1994 | Dow | A61B 8/06 310/17 |
| 5,497,776 A | * | 3/1996 | Yamazaki | A61B 8/12 128/916 |
| 6,036,646 A | * | 3/2000 | Barthe | A61B 8/00 128/916 |
| 6,093,150 A | * | 7/2000 | Chandler | A61B 8/12 600/459 |
| 6,569,100 B2 | * | 5/2003 | Okawa | A61B 8/12 600/445 |
| 7,481,115 B2 | * | 1/2009 | Hasegawa | A61B 8/12 600/462 |
| 7,494,469 B2 | * | 2/2009 | Bruestle | A61B 8/14 367/119 |
| 7,819,809 B2 | * | 10/2010 | Kim | F16H 19/005 600/459 |
| 8,162,832 B2 | * | 4/2012 | Matsuzawa | A61B 8/14 600/437 |
| 8,430,103 B2 | * | 4/2013 | Wei | A61N 1/3968 128/897 |
| 8,926,533 B2 | * | 1/2015 | Bockenstedt | A61N 7/02 601/2 |
| 9,017,262 B2 | * | 4/2015 | Bruestle | A61B 8/4444 600/459 |
| 9,180,490 B2 | * | 11/2015 | Tai | A61B 8/4494 |
| 9,763,643 B2 | * | 9/2017 | Choi | A61B 8/4494 |
| 9,808,220 B2 | * | 11/2017 | Choi | A61B 8/08 |
| 9,962,140 B2 | * | 5/2018 | Song | A61B 8/4461 |
| 10,080,546 B2 | * | 9/2018 | Park | A61B 8/4488 |
| 10,362,927 B2 | * | 7/2019 | Grant | A61B 1/05 |
| 2005/0090740 A1 | * | 4/2005 | Raitzer | A61B 8/12 600/437 |
| 2005/0124887 A1 | * | 6/2005 | Li | A61B 8/4461 600/443 |
| 2006/0191345 A1 | | 8/2006 | Hasegawa et al. | |
| 2006/0241424 A1 | * | 10/2006 | Akiyama | A61B 8/483 600/437 |
| 2006/0241453 A1 | * | 10/2006 | Nguyen-Dinh | A61B 8/483 600/445 |
| 2008/0307888 A1 | * | 12/2008 | Yoshioka | B60Q 1/0023 73/627 |
| 2010/0156404 A1 | * | 6/2010 | Han | A61B 8/12 324/251 |
| 2010/0234734 A1 | * | 9/2010 | Cho | A61B 8/4281 600/459 |
| 2011/0071398 A1 | * | 3/2011 | Hwang | A61B 8/445 600/459 |
| 2011/0071399 A1 | * | 3/2011 | Tang | A61B 8/00 600/459 |
| 2011/0201937 A1 | * | 8/2011 | Fujii | A61B 8/14 600/459 |
| 2011/0224551 A1 | * | 9/2011 | Barnard | A61B 8/56 600/445 |
| 2012/0269676 A1 | * | 10/2012 | Houser | A61B 17/320068 422/1 |
| 2013/0172751 A1 | | 7/2013 | Heinrich et al. | |
| 2013/0207517 A1 | * | 8/2013 | Naka | A61B 8/546 310/334 |
| 2019/0159758 A1 | * | 5/2019 | Hwang | A61B 8/4461 |

OTHER PUBLICATIONS

Chinese Office Action dated May 21, 2020 issued in Chinese Patent Application No. 201610838772.1 (with English translation).

Chinese Office Action dated Feb. 7, 2021 issued in Chinese Patent Application No. 201610838772.1 (with English translation).

* cited by examiner

ULTRASONIC PROBE

CROSS-REFERENCE TO RELATED APPLICATION

This application claims the benefit of the Korean Patent Application No. 10-2015-0149107, filed on Oct. 27, 2015, in the Korean Intellectual Property Office, the disclosure of which is incorporated herein by reference.

BACKGROUND

1. Field

Embodiments of the present disclosure relate to an ultrasonic probe to obtain ultrasonic images.

2. Description of the Related Art

An ultrasonic imaging apparatus is an apparatus configured to radiate ultrasonic signals toward a target portion at an inside of a body from a surface of the body of a subject, and obtain images related to a cross section of a soft tissue or a blood flow by use of the information of the reflected ultrasonic signals, that is, ultrasonic echo signals, through a non-invasive method.

The ultrasonic imaging apparatus, when compared to other image diagnosis apparatuses such as an x-ray diagnostic apparatus, an x-ray Computerized Tomography Scanner, a Magnetic Resonance Image (MRI), and a nuclear medicine diagnosis apparatus, is provided in a small size and less costly, while capable of displaying in real time basis, and is provided with high stability while less exposed to radiation, and thus is widely used in diagnosis of hearts, abdomens, urinary systems, and in gynecology.

SUMMARY

Therefore, it is an aspect of the present disclosure to provide an ultrasonic probe capable of preventing inside components from being damaged by an outside impact.

Additional aspects of the disclosure will be set forth in part in the description which follows and, in part, will be obvious from the description, or may be learned by practice of the disclosure.

In accordance with one aspect of the present disclosure, an ultrasonic probe includes a transducer rotatably provided; a shaft at which the transducer is mounted; and a supporting member rotatably supporting the shaft, and the supporting member is provided with a buffer unit to mitigate an outside impact.

The buffer unit may be provided by forming a hole at one side of the supporting member.

The buffer unit may be provided by bending the supporting member such that a portion of the supporting member forms a curved surface.

The buffer unit may be provided using material having elasticity and mounted at the supporting member.

The supporting member may be provided using material having elasticity.

The buffer unit may be provided to be deformed by an outside impact and returned to an original state when the outside force is removed.

The supporting member may include a first supporting unit at which the shaft is mounted, and a second supporting unit fixed to a base frame.

The buffer unit may be provided in the shape of a hole that is formed at the second supporting unit.

The first supporting unit may be connected to the second supporting unit by a connection unit.

The buffer unit may be an elastic member mounted at the connection unit and elastically supporting the first supporting unit and the second supporting unit.

The connection unit and the elastic member each may be provided in plural.

The first supporting unit, the second supporting unit, and the connection unit may be integrally formed with one another.

The first supporting unit may be provided with an insertion hole into which the shaft is inserted.

The buffer unit may be provided between an inner side surface of the first supporting unit forming the insertion hole and the shaft.

The buffer unit may include an elastic member provided in the shape of a ring.

In accordance with another aspect of the present disclosure, an ultrasonic probe includes a transducer, a shaft, a supporting member, and a base frame. The transducer may be configured to transmit/receive ultrasonic waves. The shaft may have the transducer mounted thereat and configured to rotate by a driving force received from a driving source. The supporting member may be configured to rotatably support the shaft. The base frame may have the supporting member fixed thereto. The supporting member may be provided with a buffer unit having an elasticity as to prevent deformation of the shaft or the supporting member by mitigating an impact applied to the shaft or the supporting member.

The buffer unit may be provided by forming a hole at one side of the supporting member.

The buffer unit may be provided by mounting an elastic member at one side of the supporting member.

The buffer unit may be provided by bending the supporting member to form a curved surface.

The supporting member may be provided with an insertion hole into which the shaft is rotatably inserted.

The buffer unit may be positioned in between an inner side surface of the supporting member forming the insertion hole and an outer side surface of the shaft.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
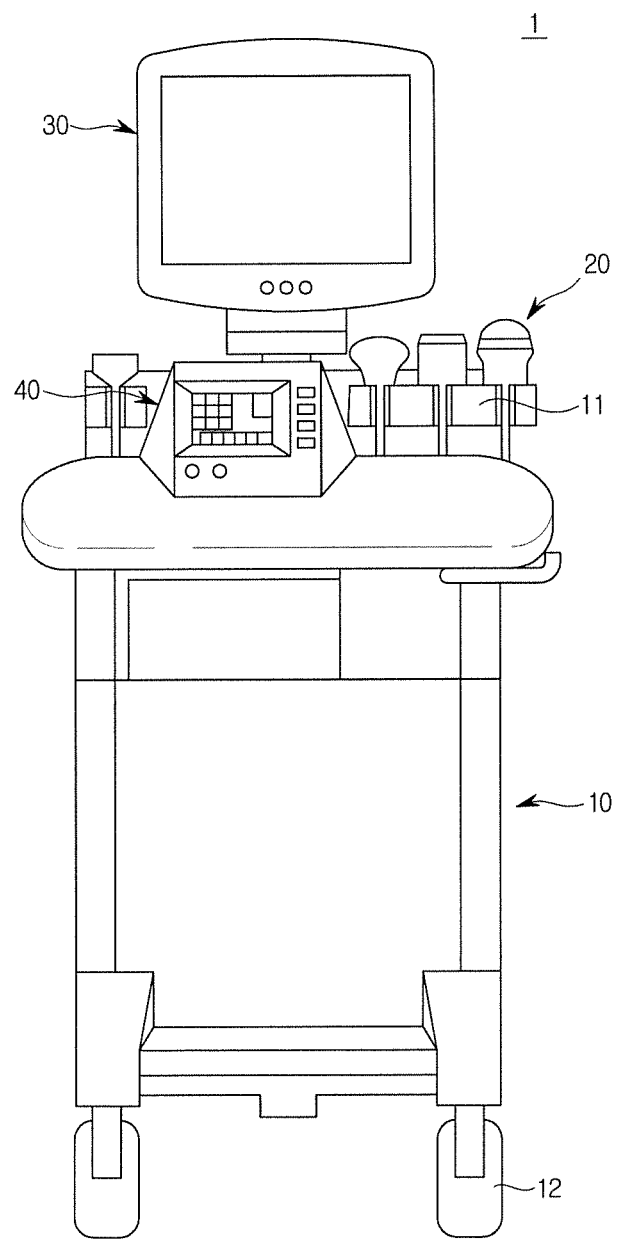
FIG. 1 is a drawing illustrating an ultrasonic imaging apparatus according to one embodiment of the present disclosure.

Reference will now be made in detail to the embodiments of the present disclosure, examples of which are illustrated in the accompanying drawings, wherein like reference numerals refer to like elements throughout.

FIG. 1 is a drawing illustrating an ultrasonic imaging apparatus according to one embodiment of the present disclosure.

Referring to FIG. 1, an ultrasonic imaging apparatus 1 according to one embodiment of the present disclosure includes a body 10, and a probe 20 to transmit ultrasonic signals at a subject to be diagnosed and to receive the reflected ultrasonic signals from the subject. The probe 20 may be connected to the body 10 by use of a cable.

The body 10 may be provided with a display 30 to display diagnostic results obtained from the received ultrasonic signals. The display 30 may be provided with applications related to the motions of the ultrasonic imaging apparatus 1 displayed thereto. As one example, the display 30 may be provided with the information related to the ultrasonic images obtained in the process of an ultrasonic diagnosis or the motions of the ultrasonic imaging apparatus 1 displayed thereto.

The display 30 may be implemented in the form of a Cathode Ray Tube (CRT) or a Liquid Crystal Display (LCD). The display 30 may be provided in a plurality of units. In a case when the display 30 is provided in a plurality of units, the display 30 may include a main display and a sub display. As one example, the main display may be provided with ultrasonic images obtained in an ultrasonic diagnostic process displayed thereto, and the sub display may be provided with the information related to the motions of the ultrasonic imaging apparatus displayed thereto.

The body 10 may be provided with in input unit 40. The input unit 40 may be provided in the form of a keyboard, a foot switch, or a foot pedal. In a case when the input unit 40 is provided in the form of the keyboard, the keyboard may be provided at an upper portion of the body 10. In a case when the input unit 40 is provided in the form of the foot switch or the foot pedal, the foot switch or the foot pedal may be provided at a lower portion of the body 10. An administrator may control the motions of the ultrasonic imaging apparatus 1 through the input unit 40.

The body 10 may be provided with a moving apparatus 12 as to move the ultrasonic imaging apparatus 1. The moving apparatus 12 may be a plurality of casters provided at a lower surface of the body 10. The casters may be aligned as to drive the body 10 in a predetermined direction, or locked as to stop the body 10 at a predetermined position.

Figure 2:
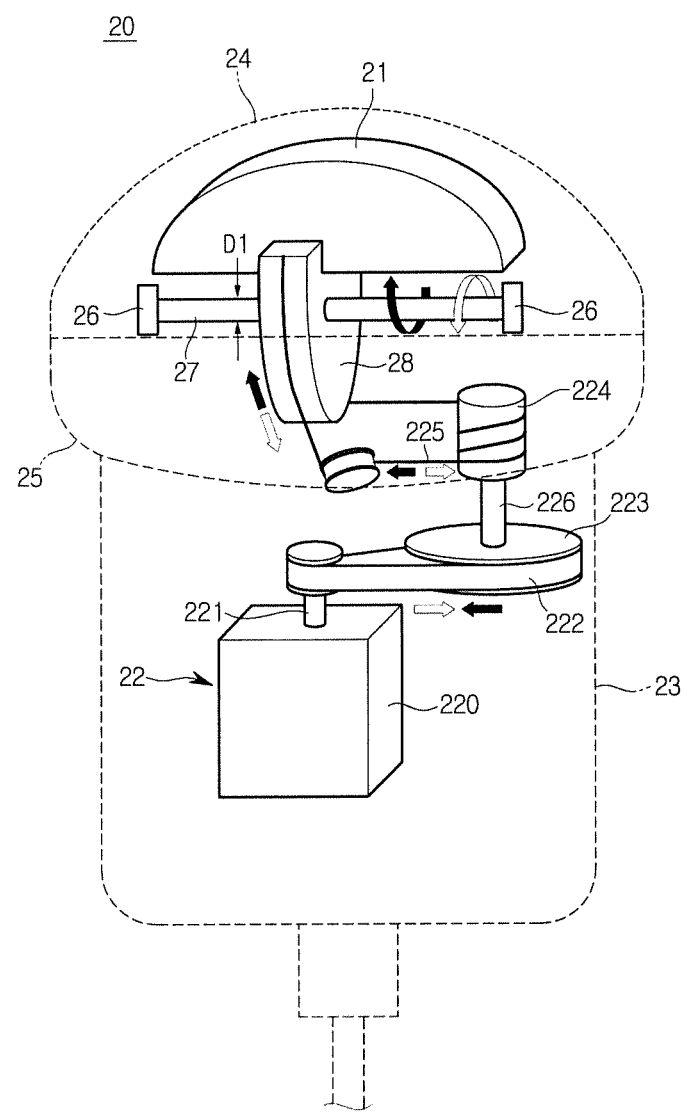
FIG. 2 is a drawing illustrating a probe according to one embodiment of the present disclosure.

FIG. 2 is a drawing illustrating a probe according to one embodiment of the present disclosure.

Referring to FIG. 2, a probe 20 according to one embodiment of the present disclosure includes a transducer 21 rotatably provided. The probe 20 may be provided with a handle case 23 provided as to use the transducer 21 as a user grasps the handle case 23. A front end of the handle case 23 may be provided with a cap 24 disposed thereto as the cap 24 is adjacent to a subject to be diagnosed. The transducer 21 may be provided at an inside of the cap 24.

The transducer 21 may include an ultrasonic oscillator to transmit and receive ultrasonic waves. The transducer 21 may be rotatably installed at an inside of the cap 24, and may read three-dimensional images of the subject to be diagnosed.

The transducer 21 may be mounted at a shaft 27. The shaft 27 may be rotated while transferred with a driving force from a driving apparatus 22. As the shaft 27 is rotated, the transducer 21 mounted at the shaft 27 may be rotated together.

The cap 24 may be provided with an inner surface corresponding to an outer surface of the transducer 22 such that the gap between the inner surface of the cap 24 and the outer surface of the transducer 21 may be steadily maintained even in a case when the transducer 21 installed at an inside of the cap 24 is rotated. As one example, the outer surface of the transducer 21 and the inner surface of the cap 24 each may be provided in the shape of a ring having an identical central portion.

An inside space of the cap 24 may be filled with oil configured to perform a role as a medium to have the ultrasonic waves generated at the transducer 21 transferred. A base frame 25 may be provided in between the cap 24 and the handle case 23 as to divide an inside space of the cap 24 and an inside space of the handle case 23. The oil may be filled in a space 200 formed by use of the cap 24 and the base frame 25.

The shaft 27 may be rotated while transferred with a driving force from the driving apparatus 22. The driving apparatus 22 may be accommodated at an inside of the handle case 23. The driving apparatus 22 may include a driving motor 220, pulleys 221, 223, and 224 configured to be transferred with a driving force from the driving motor 220, and wires 222 and 225 to transfer the driving force of the driving motor 220.

A first pulley 221 may be rotated while transferred with the driving force of the driving motor 220. A first wire 222 may connect the first pulley 221 and a second pulley 223. The driving force transferred to the first pulley 221 by use of the first wire 222 may be transferred to the second pulley 223.

The second pulley 223 and a third pulley 224 may be connected by use of a transfer unit 226. As one example, the transfer unit 226 may be a shaft connecting the second pulley 223 and the third pulley 224. The second pulley 223 and the third pulley 224 may be fixed to one end portion and the other end portion of the shaft, respectively. As the above, the third pulley 224 may be rotated along with the second pulley 223 as the second pulley 223 is rotated while transferred with a driving force.

The type of the transfer unit 226 is not limited to a shaft. The transfer unit 226 may be adequately structured according to an inside structure of an inside of the handle case 23. The transfer unit 226 may be provided with a structure having the pulleys and the wires, or may be provided with a structure by use of a gear connection.

Hereinafter, an embodiment in which the second pulley 223 and the third pulley 224 are connected by use of the shaft will be described. As the second pulley 223 is rotated while transferred with a driving force, the third pulley 224 may be rotated along with the second pulley 223.

The shaft 27 may be provided with a driving force transferring member 28 mounted thereto. The driving force transferring member 28 may be rotated along with the shaft 27 while fixed to one side of the shaft 27. The driving force transferring member 28 and the third pulley 224 may be connected by use of a second wire 225. As the third pulley 224 is rotated, the driving force transferring member 28 may be rotated as the rotational force is transferred by use of the second wire 225. At this time, the shaft 27 may be rotated along with the driving force transferring member 28.

The second wire 225 may be wound at the third pulley 224, and may be provided to wrap around a portion of an outer circumferential surface of the driving force transferring member 28. One end portion of the second wire 225 may be connected to a first elastic portion (not shown), and the other end portion of the second wire 225 may be connected to a second elastic portion (not shown). As the second wire 225 wound at the driving force transferring member 28 is connected to the elastic portions (not shown), even when the driving force transferring member 28 is rotated, the tension of the second wire 225 may be maintained. Therefore, a loosening of the second wire 225 from the rotation of the driving force transferring member 28 may be prevented.

The shaft 27 may be rotatably mounted at a supporting member 26. The supporting member 26 may be protruded from the base frame 25. The shaft 27 may be rotated in one direction or the other direction while transferred with a driving force from the driving apparatus 22 as the shaft 27 is mounted at the supporting member 26. The supporting member 26 may include a first supporting member 26a provided at one end portion side of the shaft 27, and a second supporting member 26b provided at the other end portion side of the shaft 27.

Figure 3:
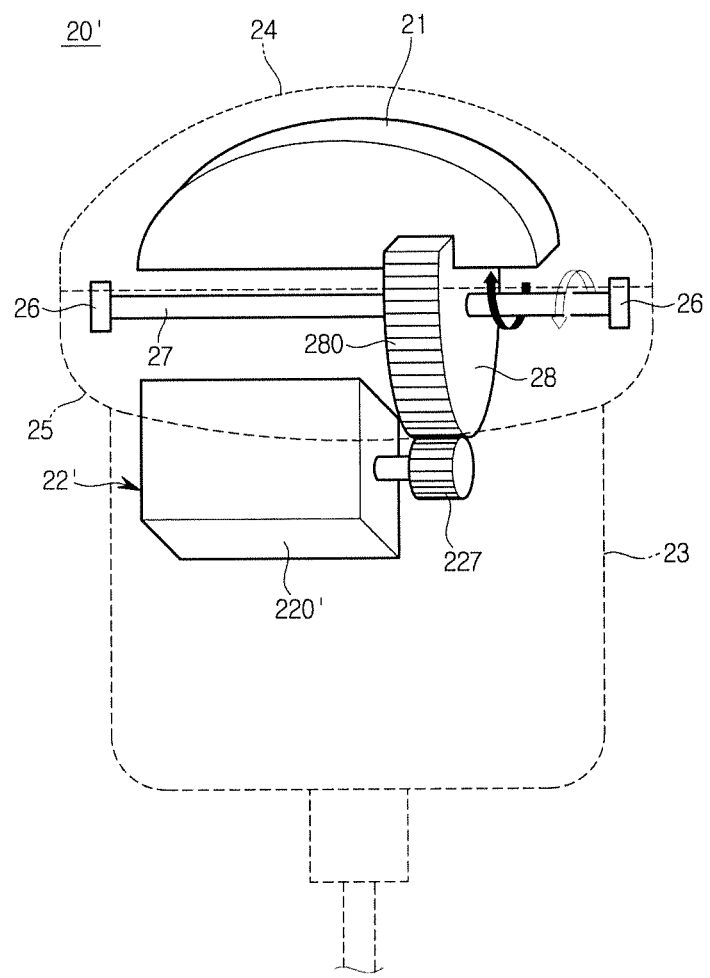
FIG. 3 is a drawing illustrating a probe according to another embodiment of the present disclosure.

FIG. 3 is a drawing illustrating a probe according to another embodiment of the present disclosure.

Referring to FIG. 3, the driving force of a driving force 22' of a probe 20' according to another embodiment of the present disclosure may be transferred to the shaft 27 by use of a gear connection. A driving motor 220' may be provided with a rotating gear 227 configured to rotate by use of the driving force of the driving motor 220'. An outer circumferential surface of a driving force transferring member 28' may be provided with a gear unit 280 teeth-coupled to the rotating gear 227.

As the rotating gear 227 is rotated in a clockwise direction by use of the driving motor 220', the driving force transferring member 28' may be rotated in a counter-clockwise direction. As the rotating gear 227 is rotated in a counter-clockwise direction by use of the driving motor 220', the driving force transferring member 28' may be rotated in a clockwise direction. The shaft 27 may be rotated in a clockwise direction or a counter-clockwise direction along with the driving force transferring member 28'.

The structure other than the driving apparatus 22' may be applied similarly to the structure of the probe 20 illustrated on FIG. 2. Hereinafter, the structure of the supporting member 26 of the probe 20 disclosed on FIG. 2 will be described. The probe 20' disclosed on FIG. 3 may be provided with the hereinafter descriptions similarly applied hereto.

Figure 4:
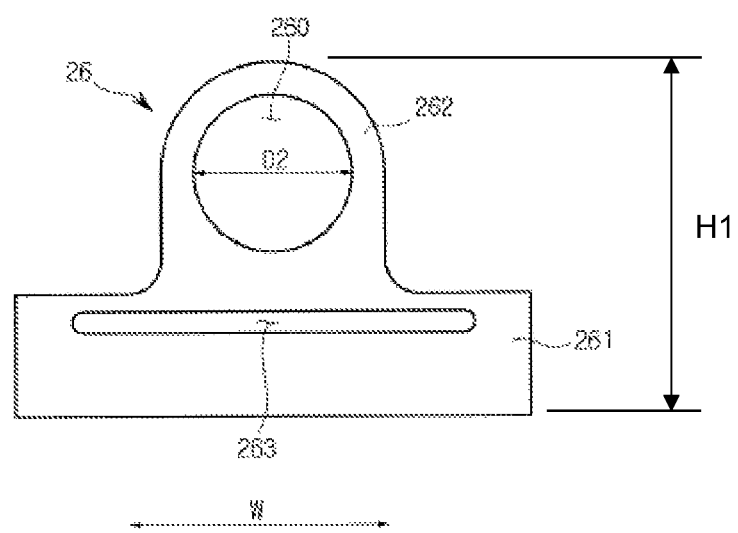
FIG. 4 is a drawing illustrating a supporting member according to one embodiment of the present disclosure.

FIG. 4 is a drawing illustrating a supporting member according to one embodiment of the present disclosure.

Referring to FIG. 4, the supporting member 26 according to one embodiment of the present disclosure may include a first supporting unit 261 mounted at the base frame 25, and a second supporting unit 262 at which the shaft 27 is mounted. The first supporting unit 261 and the second supporting unit 262 may be integrally formed with one another.

The supporting member 26 may be provided with metallic material having the hardness to support the shaft 27, and configured to be flexibly responsive with respect to an outside impact. As one example, the supporting member 26 may be provided with metallic material, including aluminum.

The second supporting member 262 may be provided with an insertion hole 260 into which the shaft is inserted formed thereto. The shaft 27 may be insertedly fixed to the insertion hole 260. The diameter D2 of the insertion hole 260 may be identical to or somewhat larger than the diameter D1 of the shaft 27.

The first supporting member 261 may be provided with a buffer unit 263 configured to ease the impact applied to the supporting member 26. While using the probe 20, even when an impact is applied to the cap 24 as the probe 20 is dropped by a user, the impact is eased by use of the buffer unit 263, and the inside components of the probe 20 being damaged by the displacement of the shaft 27 may be prevented.

The buffer unit 263 may be provided in the shape of a hole formed at the first supporting unit 261. The hole may be formed lengthways in a width direction W of the first supporting unit 261. On FIG. 4, the buffer unit 263 is formed in the shape of a hole formed lengthways in the width direction W of the first supporting unit 261, but the shape or the number of the hole is not limited hereto, and may be formed in various shapes and numbers.

Figure 5:
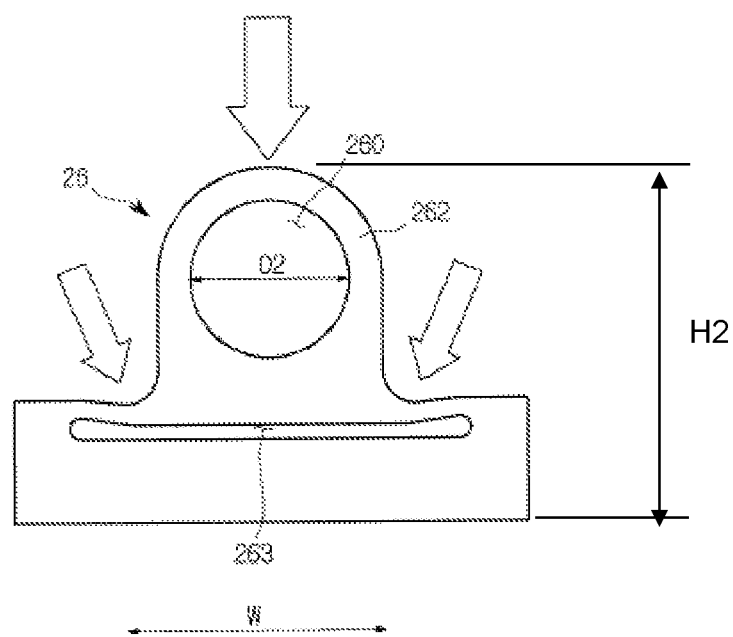
FIG. 5 is a drawing illustrating an image when an impact is applied to the supporting member according to one embodiment of the present disclosure.
Figure 6:
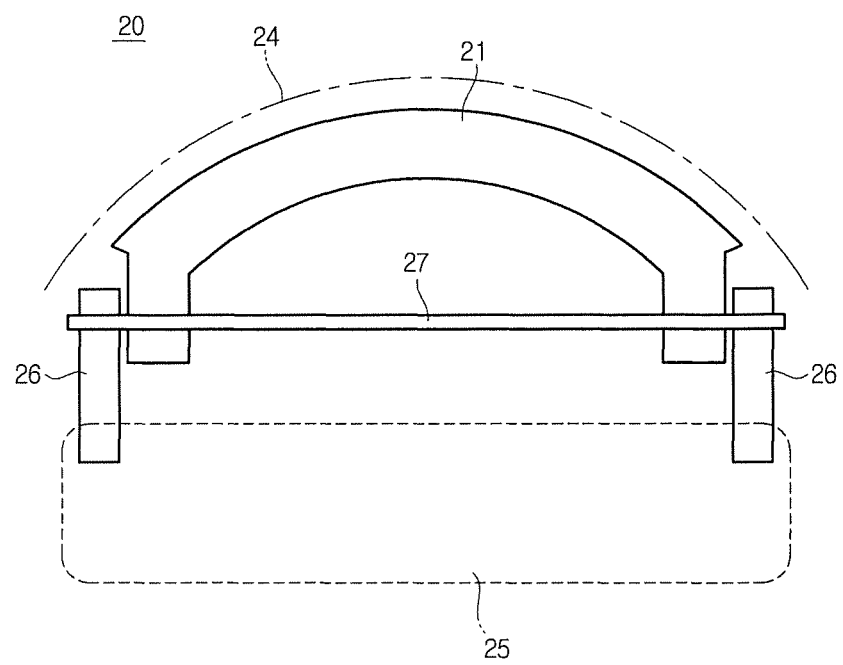
FIG. 6 and FIG. 7 are drawings illustrating images before and after an impact is applied to the probe according to one embodiment of the present disclosure.
Figure 7:
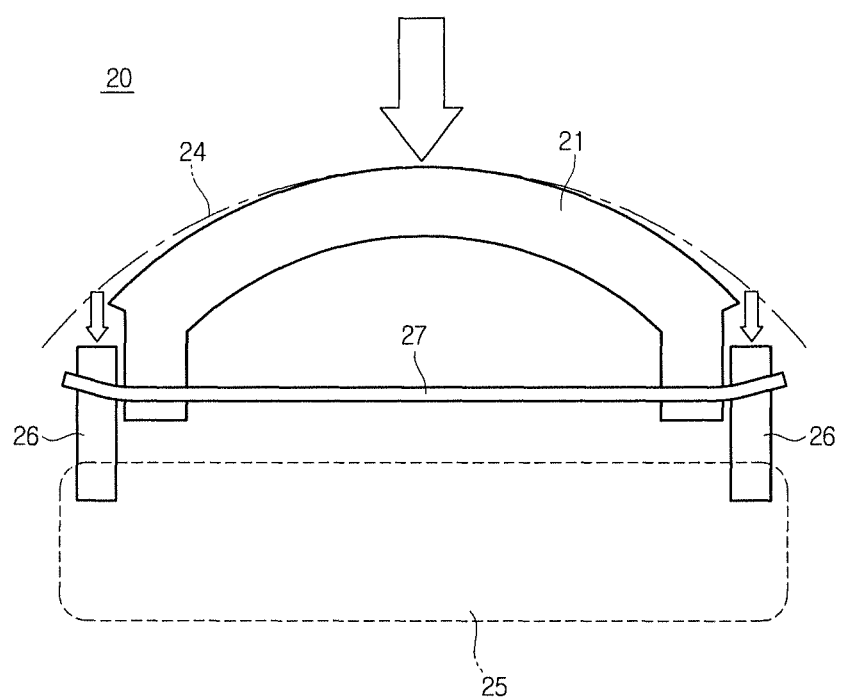

FIG. 5 is a drawing illustrating an image when an impact is applied to the supporting member according to one embodiment of the present disclosure, and FIG. 6 and FIG. 7 are drawings illustrating images before and after an impact is applied to the probe according to one embodiment of the present disclosure.

Referring to FIG. 5 to FIG. 7, when an outside impact is applied to the probe 20, the impact applied to the supporting member 26 and the shaft 27 may be eased by use of the buffer unit 263. As the impact applied to the supporting member 26 and the shaft 27 is eased by use of the buffer unit 263, the central axis of rotation of the transducer 21 may be prevented from being changed or the components provided at an inside of the cap 24 may be prevented from being damaged.

In a case when the buffer 263 is not provided, when an impact is applied to the cap 24, a collision of the cap 24 and the transducer 21 may be occurred. The shaft 27 at which the transducer 21 is mounted may be pressed by the impact of the cap 24 and the transducer 21. The supporting member 26 may be pressed toward a side of the base frame 25 by the shaft 27, and a deformation may be occurred by the force applied.

As the deformation of the supporting member 26 is occurred, the central axis of rotation of the shaft 27 at which the transducer 21 is mounted may be changed. As the central axis of rotation of the shaft 27 is changed, the central axis of rotation of the transducer 21 may also be changed. As the central axis of rotation of the transducer 21 is changed, the ultrasonic images obtained by use of the transducer 21 may be different from the ultrasonic images obtained by use of the transducer 21 prior to when the impact is applied to the probe 20. Therefore, after an impact is applied to the probe 20, the reliability of the ultrasonic images by use of the transducer 21 may be decreased. In addition, component damage may be occurred as the contact is made between the inside components as a result of the deformation of the supporting member 26 and the shaft 27.

However, in a case when the buffer unit 263 is provided at the supporting member 26, even when an outside impact is applied to the probe 20, the impact may be eased by use of the buffer unit 263, so that the reliability of the ultrasonic images may be prevented from being decreased or the inside component may be prevented from being damaged.

When an impact is occurred between the cap 24 and the transducer 21 as the impact is applied to the probe 20, the force applied to the supporting member 26 through the transducer 21 may be transferred after being eased by use of the buffer unit 263. The supporting member 26 may be provided with the shape thereof temporarily deformed by the force applied, but by the use of the buffer unit 263, the supporting member 26 may be restored to a state prior to the force being applied. Therefore, the axial deformation of the shaft 27 may not be occurred before and after an impact is applied to the probe 20, and the inside component may be prevented from being damaged by the impact.

That is, when an outside impact is applied to the transducer 21, the impact applied to the supporting member 26 may be eased as the shape of the hole provided at the first supporting unit 261 is deformed. As illustrated on FIG. 5 to FIG. 7, the shape of the hole may be deformed by the outside impact. As the hole is pressed by the impact applied to an upper portion side of the second supporting unit 262, the height H2 of the supporting member 26 when the impact is applied may be further lower when compared to the height H1 of the supporting member 26 before the impact is applied.

When the outside force applied to the supporting member 26 is removed, the supporting member 26 may be restored to a state prior to the impact being applied. The shape of the hole may be restored to an original state prior to the impact being applied, and the height of the supporting member 26 may be returned to the height H1 prior to the impact being applied.

As the above, as the shape of the hole provided at the first supporting unit 261 is changed, the impact applied to the supporting member 26 is eased, and the deformation of the supporting member 26 may be prevented. Therefore, the central axis of rotation of the shaft 27 may be steadily maintained, and the quality of the ultrasonic images by use of the transducer 21 may be steadily maintained.

Figure 8:
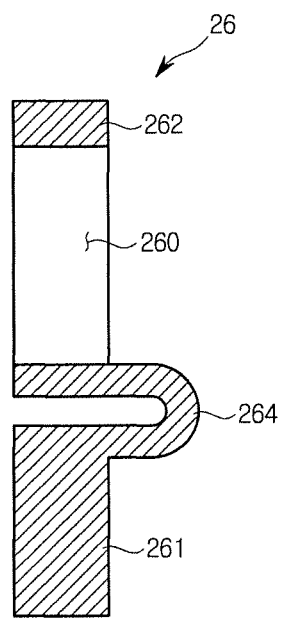
FIG. 8 to FIG. 10 are side-sectional drawings illustrating the embodiments of the supporting members.
Figure 9:
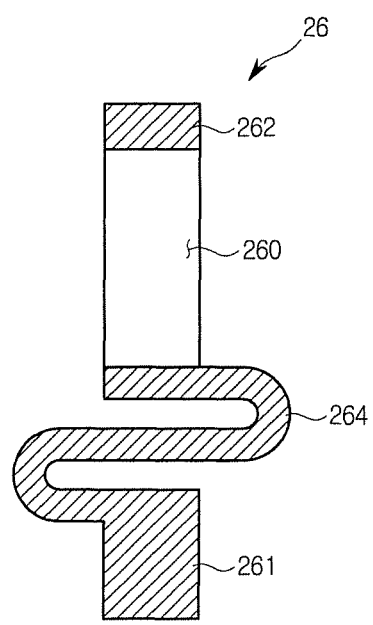
Figure 10:
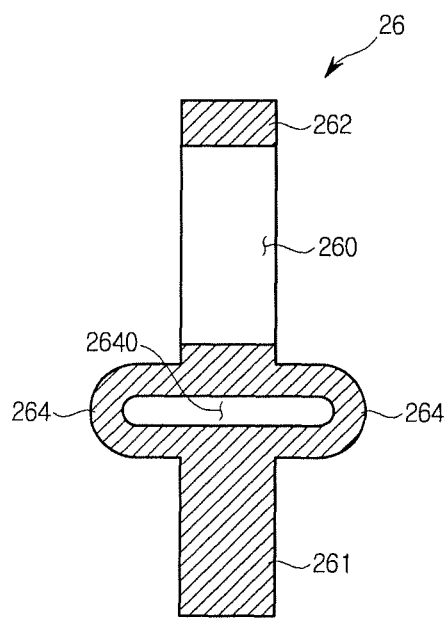

FIG. 8 to FIG. 10 are side cross-sectional drawings illustrating the embodiments of the supporting members.

Referring to FIG. 8 to FIG. 10, the first supporting unit 261 and the second supporting unit 262 of the supporting member 26 may be connected by use of a connection unit 264. The connection unit 264 may perform a role as a buffer unit configured to ease the impact applied to the supporting member 26 while provided in various shapes.

Referring to FIG. 8 to FIG. 10, the connection unit 264 may connect the in between of the first supporting unit 261 and the second supporting unit 262 by means of bypassing as to be provided with a curved surface. That is, the connection unit 264 may be provided to be longer than the shortest distance between the first supporting unit 261 and the second supporting unit 262. That is, the connection unit 264 may be bent to form a curved surface.

As illustrated on FIG. 8, the connection unit 264 may be connected to the second supporting unit 262 from the first supporting unit 261 after bypassing in a front direction or a rear direction of the connection unit 264. As illustrated on FIG. 9, the connection unit 264 may be provided to be bypassing the in between of the first supporting unit 261 and the second supporting unit 262 at least twice in front and rear directions. In addition, as illustrated on FIG. 10, the connection unit 264 by connecting the in between of the first supporting unit 261 and the second supporting unit 262 by bypassing in the front and rear directions, may be provided such that an empty space 2640 may be formed at an inside of the connection unit 264.

Here, the front direction and the rear direction are referred to as the front direction and the rear direction of the supporting member 26 while having a direction directly facing the front of the insertion hole 260, into which the shaft 27 is inserted, as a reference.

The connection unit 264 may be provided with a predetermined elasticity while provided with the length thereof that is longer than the shortest distance between the first supporting unit 261 and the second supporting unit 262 and provided to connect the in between of the first supporting unit 261 and the second supporting unit 262 by bypassing in the front and rear directions. As the above, the connection unit 264 may elastically support the first supporting unit 261 and the second supporting unit 262. The connection unit 264 may perform a role as a buffer unit to mitigate the force applied to the supporting member 26.

When an impact is applied to the probe 20 as when the probe 20 is descended by the carelessness of a user and when an impact is occurred in between the cap 24 and the transducer 21, the force applied to the supporting member 26 through the transducer 21 may be buffered by use of the connection unit 264 provided to perform a role as a buffer unit. The connection unit 264 may be provided with the shape thereof temporarily deformed by an outside force, but may be restored by use of an elastic force when the outside force is removed. Therefore, the axial deformation of the shaft 27 may not be occurred before and after an impact is applied to the probe 20, and the inside component may be prevented from being damaged by the impact.

The embodiment in which the connection unit 264 is provided to have elasticity by use of the shape thereof is not limited to the illustrations provided on FIG. 8 to FIG. 10. The connection unit 264 may be provided to perform a role as a buffer unit to mitigate an outside impact while provided in various shapes.

Figure 11:
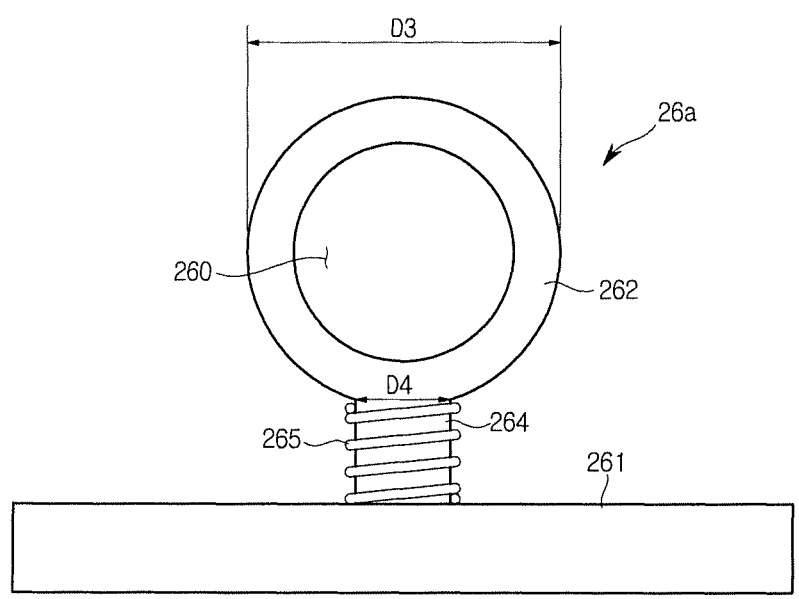
FIG. 11 and FIG. 12 are drawings illustrating a supporting member according to another embodiment of the present disclosure.
Figure 12:
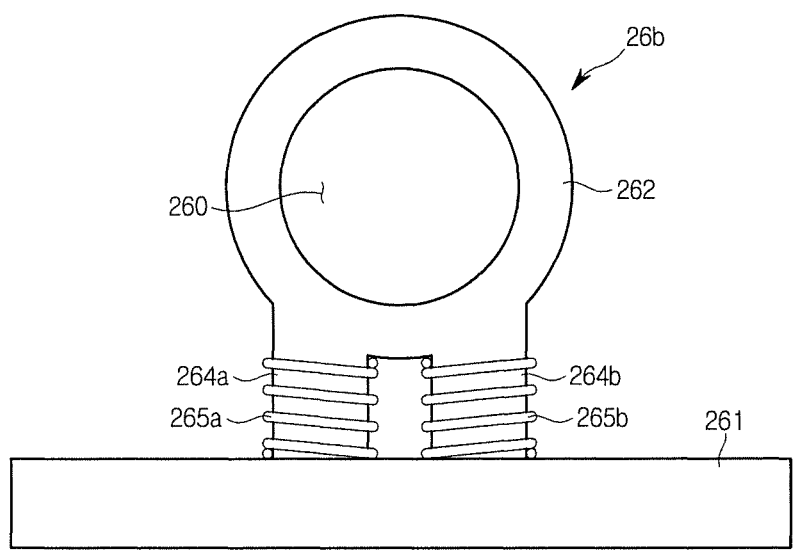

FIG. 11 and FIG. 12 are drawings illustrating a supporting member according to another embodiment of the present disclosure.

Referring to FIG. 11 and FIG. 12, supporting members 26a and 26b according to another embodiment of the present disclosure may be provided with connection units 264, 264a and 264b connecting in between of the first supporting unit 261 and the second supporting unit 262. The connection unit 264, 264a, and 264b may be provided with elastic members 265, 265a, and 265b as to elastically support the first supporting unit 261 and the second supporting unit 262. The diameter of the each of the connection units 264, 264a, and 264b may be provided to be smaller than the diameter D3 of the first supporting member 261.

As illustrated on FIG. 11, the first supporting unit 261 and the second supporting unit 262 of the supporting member 26a may be connected by use of the single connection unit 264. The connection unit 264 may be provided with the elastic member 265. The elastic member 265 may elastically support the first supporting unit 261 and the second supporting unit 262.

When an outside impact is applied to the probe 20 and when an impact is occurred in between of the cap 24 and the transducer 21, the force applied to the supporting member 26a through the transducer 21 may be buffered by use of the elastic member 265. That is, the elastic member 265 may perform a role as a buffer unit.

The supporting member 26a may be provided with the shape thereof temporarily deformed by the force applied, but by the use of the elasticity of the elastic member 265, the supporting member 26a may be restored to a state prior to the force being applied. Therefore, the axial deformation of the shaft 27 may not be occurred before and after an impact is applied to the probe 20, and the inside component may be prevented from being damaged by the impact.

Figure 13:
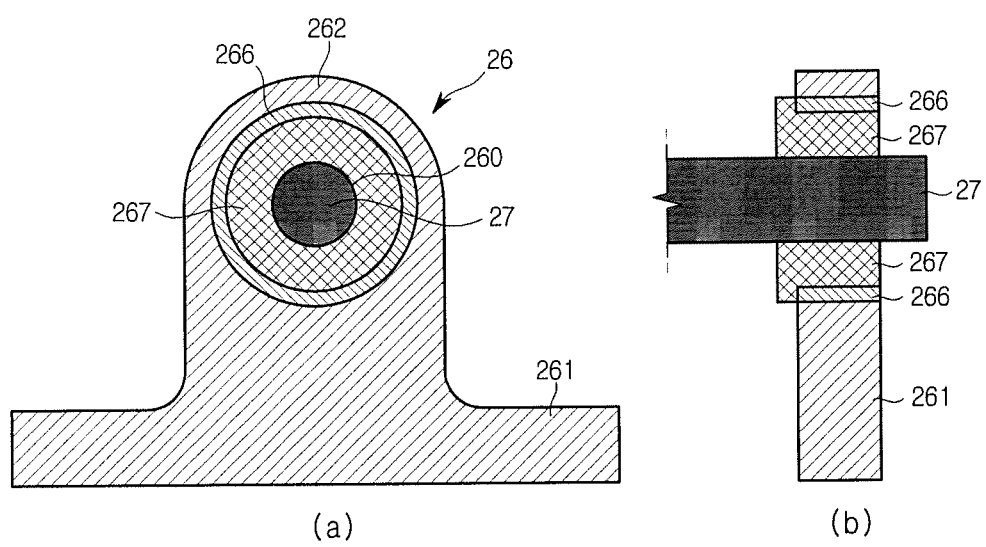
FIG. 13 is a drawing illustrating a supporting member according to still another embodiment of the present disclosure.

As illustrated on FIG. 13, the first supporting unit 261 and the second supporting unit 262 of the supporting member 26b may be connected by use of the plurality of connection units 264a and 264b. On FIG. 9, the first supporting unit 261 and the second supporting unit 262 are illustrated to be connected by use of the two units of the connection units 264a and 264b while the connection units 264a and 264b are spaced apart with respect to each other, but the number of the connection units is not limited to the illustration provided on FIG. 9.

The plurality of connection units 264a and 264b may be provided with the elastic members 265a and 265b mounted thereto, respectively. The connection units 264a and 264b includes a first connection unit5 264a and a second connection unit 264b, the first connection unit 264a may be provided with a first elastic member 265a mounted thereto, and the second connection unit 264b may be provided with a second elastic member 265b mounted thereto. The first elastic member 265a and the second elastic member 265b may elastically support the first supporting unit 261 and the second supporting unit 262.

As described on FIG. 11, in a case when an impact is applied to the probe 20 as the probe 20 is dropped by a user, the impact applied to the supporting member 26 through the transducer 21 may be buffered by use of the elasticity of the first elastic member 265a and the second elastic member 265b. Therefore, the axial deformation of the shaft 27 may not be occurred before and after an impact is applied to the probe 20, and the inside component may be prevented from being damaged by the impact.

Figure 14:
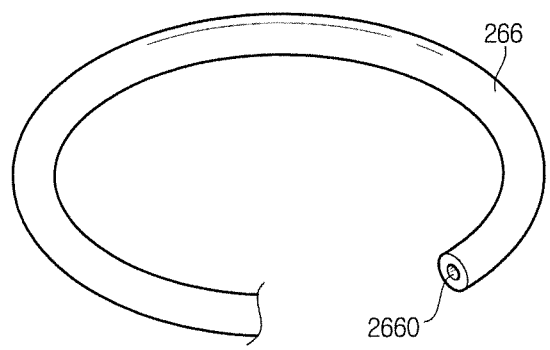
FIG. 14 to FIG. 16 are drawings illustrating the embodiments with respect to an inside image of a supporting member according to still another embodiment of the present disclosure.
Figure 15:
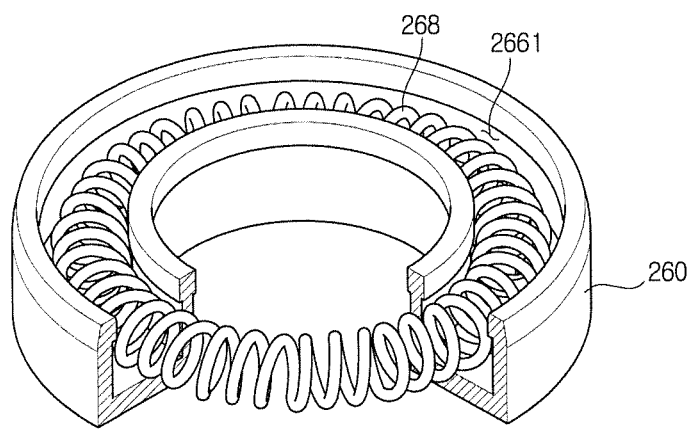
Figure 16:
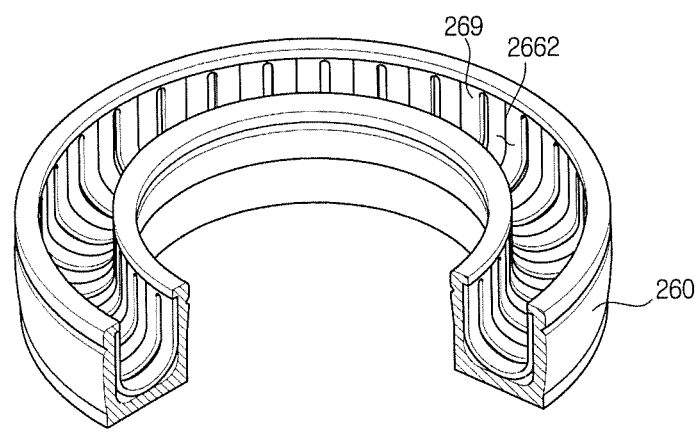

FIG. 13 is a drawing illustrating a supporting member according to still another embodiment of the present disclosure, and FIG. 14 to FIG. 16 are drawings illustrating the embodiments with respect to an inside image of a supporting member according to still another embodiment of the present disclosure.

Referring to FIG. 13 to FIG. 16, the second supporting unit 262 of the supporting member 26 may be provided with a buffer unit 266 along an inner side surface of the second supporting unit 262 forming the insertion hole 260. The buffer unit 266 may be provided with material capable of absorbing impact. As one example, the buffer unit 266 may be provided with the material having elasticity such as elastomer or plastic.

The insertion hole 260 may be provided with a bearing 267 mounted thereto as to have the rotation of the shaft 27 easily performed. The diameter of the bearing 267 may be provided to be identical to the diameter of the shaft 27. The shaft 27 may be rotatably provided while inserted into the bearing 267.

The buffer unit 266 may be provided in between of the bearing 267 and the second supporting unit 262. The buffer unit 266 may buffer the impact in between the shaft 27 and the second supporting unit 262.

As illustrated on FIG. 14, the buffer unit 266 may be provided in the shape of a ring having an empty space 2660 formed at an inside of the buffer unit 266. At this time, the buffer unit 266 may be provided with the material having elasticity such as elastomer or plastic. As the buffer unit 266 having the shape of a ring provided with the inside space 2660 formed at an inside of the buffer unit 266 is provided to mitigate an outside impact, even when an outside force is applied to the shaft 27, the force applied may be buffered, and thus the axial deformation of the shaft 27 may be prevented and the damage on the inside component by the deformation of the supporting member 26 or the shaft 27 may be prevented. The shape of the buffer unit 266 is not limited to the shape of a ring provided with an empty space formed at an inside of the buffer unit 266.

As illustrated on FIG. 15, the buffer unit 266 is provided with an empty space 2662 formed at an inside of the buffer unit 266, and may be provided with a buffer member 269 provided to be positioned at an inside of the inside space 2662 as the buffer member 269 is provided with the material having elasticity. The buffer member 269 may be positioned adjacent to an inner wall forming an inside space of the buffer unit 266.

As illustrated on FIG. 14, the buffer unit 266 may be provided in the shape of a ring having an empty space at an inside of the buffer unit 266, or, as illustrated on FIG. 15 and FIG. 16, the buffer unit 266 may be provided in the shape in which an elastic part 268 or the buffer member 269 is accommodated at an inside space of the buffer unit 266 while one side surface of the buffer unit 266 is provided in an open shape. The buffer unit 266 may buffer the outside force applied to the supporting member 26 or the shaft 27 while disclosed in between the shaft 27 and the bearing 267 mounted at a side of the insertion hole 260 as the buffer unit 266 is provided to have elasticity.

As the above, by use of the structure of the supporting member 26, when an impact is applied to the probe 20, an occurrence of an axial deformation of the shaft 27 or a damage of the inside component by the deformation of the supporting member 26 or the shaft 27 may be prevented. Accurate ultrasonic images may be obtained by preventing the damage on the probe 20.

As is apparent from the above, the ultrasonic probe according to one aspect of the present disclosure can mitigate an outside impact while provided with a buffer unit at a supporting member. Accordingly, the components provided at an inside of the ultrasonic probe can be prevented from being damaged. With the above, the quality of ultrasonic images can be prevented from being lowered by an outside impact.

Although a few embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:
1. An ultrasonic probe, comprising:
a rotatable transducer;
a shaft having the transducer mounted thereto; and
a supporting member rotatably supporting the shaft and having an insertion hole into which the shaft is inserted,
wherein the supporting member includes a buffering hole penetrating the supporting member,
wherein the buffering hole is disposed below the insertion hole and the transducer is disposed above the insertion hole in a first direction that is perpendicular to an axis of the shaft,
wherein the supporting member includes material having elasticity, and
wherein the supporting member and the buffering hole are configured such that a shape of the buffering hole is deformed by an outside impact and returned to an original state when the outside impact is removed, thereby preventing the shaft from being deformed by the outside impact.

2. The ultrasonic probe of claim 1, wherein:
the buffer unit is provided by bending the supporting member such that a portion of the supporting member forms a curved surface.

3. The ultrasonic probe of claim 1, wherein:
the buffer unit is provided using material having elasticity and mounted at the supporting member.

4. The ultrasonic probe of claim 1, wherein:
the supporting member comprises a first supporting unit fixed to a base frame and a second supporting unit having the shaft mounted thereto.

5. The ultrasonic probe of claim 4, wherein:
the buffering hole is formed at the second supporting unit.

6. The ultrasonic probe of claim 4, wherein:
the first supporting unit is connected to the second supporting unit by a connection unit.

7. The ultrasonic probe of claim 6, wherein:
the buffer unit is an elastic member mounted at the connection unit and elastically supporting the first supporting unit and the second supporting unit.

8. The ultrasonic probe of claim 7, wherein:
the connection unit and the elastic member each is provided in plural.

9. The ultrasonic probe of claim 6, wherein:
the first supporting unit, the second supporting unit, and the connection unit are integrally formed with one another.

10. The ultrasonic probe of claim 4, wherein:
the first supporting unit is provided with the insertion hole.

11. The ultrasonic probe of claim 10, wherein:
the buffering hole is provided between an inner side surface of the first supporting unit forming the insertion hole and the shaft.

12. The ultrasonic probe of claim 1, wherein
the shape of the buffering hole is deformed by the outside impact to decrease a distance between the insertion hole and the buffering hole so as to lower a height of the supporting member when compared to the height of the supporting member before the outside impact is applied.

* * * * *